(12) United States Patent
Brooks et al.

(10) Patent No.: US 7,846,728 B2
(45) Date of Patent: Dec. 7, 2010

(54) TISSUE ENGINEERING IN VIVO WITH VASCULARIZED SCAFFOLDS

(75) Inventors: Mai Nguyen Brooks, Westlake Village, CA (US); James P Watson, Los Angeles, CA (US)

(73) Assignee: BioStruxs, LLC, Westlake Village, CA (US)

( * ) Notice: Subject to any disclaimer, the term of this patent is extended or adjusted under 35 U.S.C. 154(b) by 217 days.

(21) Appl. No.: 11/973,812

(22) Filed: Oct. 9, 2007

(65) Prior Publication Data

US 2008/0090292 A1    Apr. 17, 2008

Related U.S. Application Data

(60) Provisional application No. 60/851,686, filed on Oct. 13, 2006.

(51) Int. Cl.
*C12N 5/00*    (2006.01)
*A61F 2/02*    (2006.01)

(52) U.S. Cl. .................................... 435/395; 623/23.72

(58) Field of Classification Search ................. 435/395; 623/23.72
See application file for complete search history.

(56) References Cited

U.S. PATENT DOCUMENTS

| | | | |
|---|---|---|---|
| 5,716,404 A | | 2/1998 | Vacanti et al. |
| 5,759,830 A | | 6/1998 | Vacanti et al. |
| 5,770,193 A | | 6/1998 | Vacanti et al. |
| 5,804,178 A | * | 9/1998 | Vacanti et al. .............. 424/93.7 |
| 2002/0022883 A1 | | 2/2002 | Burg |
| 2002/0119180 A1 | | 8/2002 | Yelick et al. |
| 2003/0129751 A1 | * | 7/2003 | Grikscheit et al. .......... 435/378 |
| 2004/0052768 A1 | | 3/2004 | Morrison et al. |
| 2004/0126405 A1 | | 7/2004 | Sahatjian et al. |
| 2007/0059293 A1 | | 3/2007 | Atala |
| 2007/0100358 A2 | * | 5/2007 | Romero-Ortega et al. ... 606/152 |
| 2007/0299508 A1 | | 12/2007 | Morrison et al. |

OTHER PUBLICATIONS

Atala et al., Tissue-engineered autologous bladders for patients needing cystoplasty. Lancet 2006;367:1241-6.
Grikscheit et al., Tissue-engineered large intestine resembles native colon with appropriate in vitro physiology and architecture. Ann. Surg. 2003;238:35-41.
Hori et al., Tissue engineering of the small intestine by acellular collagen sponge scaffold grafting. Int. J. Artif. Organs. 2001;24:50-4.
Kim et al., Replacement of a tracheal defect with a tissue-engineered prosthesis. J. Thorac. Cardiovasc. Surg. 2004;128:124-9.
Moriya et al., Creation of luminal tissue covered with urothelium by implant. of cultured urothelial cells into the peritoneal cavity. J Urol. 2003;170:2480-5.
Suh et al., Use of omentum as an in vivo cell culture system in tissue engineering. ASAIO J. 2004;50:464-7.
Sumita et al., Performance of collagen sponge as a 3-D scaffold for tooth-tissue engineering. Biomaterials 2006;27:3238-48.
Vacanti et al, Selective cell transplantation using bioabsorbable artificial polymers as matrices. J. Pediatr. Surg. 1988;23:3-9.

* cited by examiner

*Primary Examiner*—Thaian N Ton
*Assistant Examiner*—Marcia S Noble
(74) *Attorney, Agent, or Firm*—Inskeep IP Group, Inc.

(57) ABSTRACT

The field of the present invention relates to a novel method for producing tissue or organ in a mammal by implanting in vivo a novel three dimensional biodegradable scaffold. The novel three dimensional biodegradable scaffolds overcome the barrier of developing large organs with tissue engineering.

10 Claims, 5 Drawing Sheets

Top view

Side view

TISSUE ENGINEERING IN VIVO WITH VASCULARIZED SCAFFOLDS

RELATED APPLICATIONS

The present application claims priority to U.S. Provisional Application Ser. No. 60/851,686 filed Oct. 13, 2006.

TECHNICAL FIELD

The field of the present invention relates to a novel method for producing tissue or organ in a mammal by implanting in vivo a novel three dimensional biodegradable scaffold. The novel three dimensional biodegradable scaffolds overcome the barrier of developing large organs with tissue engineering.

BACKGROUND OF THE INVENTION

Cell culture technology has become a well-established technique that is very successful in vitro under ideal laboratory conditions. With cell specific culture media, growth factors, nutrients, and temperature, almost all human cell lines have been successfully grown in the laboratory.

Scaffold technology has made multilayer tissue engineering possible as well, with multi-cell structures successfully grown in the laboratory. Despite these successes, major roadblocks still exist in translational research. As a consequence, the only organ successfully engineered to date is a urinary bladder (Atala et al., Lancet, vol. 367, p. 1241-6, 2006).

A short list of persistent problems in this area include: 1) lack of a well developed vascular supply for organogenesis; 2) tissue resorption; 3) loss of cell function; and 4) untoward side effects.

As relates specifically to item 1), almost all tissue engineering is done with non-vascularized scaffolds. Although neovascularization with capillaries occurs very reliably in scaffolds about 1 mm in thickness, most human organs are much larger than this. As a consequence, tissue engineering on scaffolds is limited in size by the lack of arterial and venous structures which do not grow as well as capillaries. In summary, vascular supply limits organ size in scaffold based tissue engineering.

As relates specifically to item 2), tissue resorption often occurs when non-vascularized grafts are transferred in human autograft transplantation. All human autografts undergo this resorption even in the absence of infection, antigen-antibody mismatch, or lack of nutrition. A list of the tissues which have been autografted with well documented resorption over time include a) fat grafts—fat grafts larger than a few mm in diameter are well documented of undergoing resorption over time. Except for small volume fat grafting transferred into multiple well vascularized tunnels, most fat grafts undergo partial resorption. The most disconcerting aspect is that the resorption rate varies widely from 20% to 90%! This makes it difficult to compensate for resorption by overgrafting with larger volumes; b) bone grafts—small, thin non-vascularized bone grafts have an excellent track record of success in human autotransplantation. Grafts larger than 6 cm in length usually do not neovascularize as well and undergo major resorption. For this reason, most large defects are reconstructed with vascularized osteocutaneous flaps. These microvascular free flaps allow for the transfer of large bone grafts up to 24 cm in length. This difference in bone graft resorption between vascularized and nonvascularized bone grafts illustrates why this issue is pivotal in the development of tissue engineering on the multi-cm scale; and c) cartilage grafts—since cartilage is one of the few human tissues that has no endogenous blood supply and is nourished only by diffusion from the surrounding perichodrium, there was great hope that cartilage grafts would be good model for tissue engineering that would not be as dependent on vascularization for success. The full-size human ear cartilage that was successfully engineered on the back of a mouse was hailed as a major breakthrough. Sadly, this ear cartilage also underwent resorption as the ear framework scaffolding resorbed. To this date, cartilage autografts are well documented as having higher resorption rates than bone grafts in nasal surgery, craniofacial surgery, joint surgery, and ear reconstruction. Small, thin grafts do well in children. Large, thick grafts in adults fare poorly.

As relates specifically to item 3), loss of cell function also occurs in autografts involving well differentiated cells such as endocrine cells, paracrine cells, epithelium with cilia, or exocrine cells. In these cases, cell function may be lost after grafting despite cell survival. Although the exact cause for this loss of function is not clearly known, lack of a complete vascular bed (arteries, capillaries and veins) in these models may be a contributing factor. Some examples of grafts that lose their function include: a) hepatocyte grafts—in many models, hepatocyte grafting has been successful but hepatic function is lost in transfer for a significant fraction of the cells; b) B-islet cell grafts—insulin producing cells have been successfully grown in the laboratory and transplanted into animal and human subjects. Despite this success, there is a major loss in insulin production by these cells; and c) dopaminergic cell grafts—the focus of research today for the treatment of Parkinson's disease has been directed towards dopaminergic cell replacement therapy. Although these highly specialized cells have been successfully cultured, transplanted into the human brain, cell function is gradually lost.

As relates specifically to item 4), untoward side effects also occur in human autografting when cell transplantation occurs in scaffolds. A few of the well documented sequelae that have stymied translational research include: a) heterotopic ossification—when osteoprogenitor cells are transferred on scaffold systems with the necessary growth factors (bone morphogenic proteins) in children, heterotopic ossification of the surrounding muscles often result in pain, muscle function loss, and disability. Heterotopic ossification is not reversible when the scaffold is removed or when the BMPs are gone. This has been major road block in pediatric translational research despite successful osteoblast cell survival with good osteoblast function; b) scar tissue formation—due to limitations on graft size, most scaffold based tissue engineered grafts develop scar tissue around the graft. This may be due in part to normal collagenesis that occurs in wound healing, but may also be due to ischemia which is a well known trigger for scar tissue formation. Foreign body reaction to the scaffold itself may also be a cause of this scar tissue formation. Regardless of the cause, scar tissue is a major factor in disrupting normal organ function. This is considered to be an important problem in hepatic cirrhosis, glomerulonephritis, interstitial lung disease, and tenosynovitis; and c) calcifications—when fat is transferred by autologous nonvascularized grafting, by pedicled flaps, or by free microvascular flap transfer, fat necrosis is a minor occurrence with major consequences. Even if only a small percentage of the fat cells undergo cell death, these dead cells undergo saponification releasing abundant long chain fatty acids from the disrupted plasma membrane. Precipitation of these long chain fatty acids with calcium results in palpable masses that appear on mammography to be microcalcifications. This artifact makes cancer surveillance difficult with mammography. As a consequence, fat grafting for breast augmentation may make future cancer detection difficult. For this reason, autologous fat grafting for cosmetic breast augmentation has been discouraged by the FDA, radiological societies, and the plastic surgery community. Fat necrosis also causes concerns when it occurs in the reconstructed breast. In this scenario, both patients and their oncologists worry that the palpable fat necrosis may be recurrent cancer. This often necessitates a biopsy to rule out this possibility.

There has been extensive research by others to develop biocompatible composites/scaffolds, etc. For example, Burg described a biocompatible composite with viscous fluid for injection into defects (US Pat. appl. 20020022883 A1 by Burg). Of course, this concept would not work for organogenesis. Sahatjian et al. proposed a three dimensional cell scaffold either as a sheet or a tube configured into various shapes (US Pat. appl. 20040126405 by Sahatjian et al.). The Harvard University group led by Vacanti proposed placing dissociated cells into a biodegradable matrix to be implanted with a tissue expander device into the breast (U.S. Pat. No. 5,716,404 by Vacanti et al.). However, cells would perish without new blood vessels, and this idea did not materialize into practical use since its issue in 1998. Vacanti et al. also reported the idea of implanting sheets of cell-matrix structure adjacent to mesentery, omentum, or peritoneum tissue (see U.S. Pat. No. 5,804,178, U.S. Pat. No. 5,770,193, and U.S. Pat. No. 5,759,830).

Yelick et al. successfully constructed a biodegradable polymer scaffold molded in the shape of a tooth and placed in onto the omentum of rats (US Pat. appl. 20020119180 A1 by Yelick et al.). A later application describes a method to achieve high density seeding of polymer scaffold with organoid units (US Pat. appl. 20030129751 by Grikscheit et al.). The disclosed scaffolds are collagen-coated 1 cm long 0.5 mm woven polyglycolic acid tubes with a diameter of 0.5 cm, that are sutured to the rat's omentum to make new colonic tissue (Grikscheit et al., Annals of Surgery, vol. 238, p. 35-41, 2003).

The omentum has been used by various investigators as a source of vasculature for tissue engineering purposes: porcine tooth (Sumita et al., Biomaterials, vol. 27, p. 3238-48, 2006), dog small intestine (Hori et al., International Journal of Artificial Organs, vol. 24, p. 50-4, 2001), dog tracheal defects (Kim et al., Journal of Thoracic and Cardiovascular Surgery, vol. 128, p. 124-9, 2004), canine oral epithelial cells and rib chondrocytes (Suh et al., ASAIO Journal, vol. 50, p. 464-7, 2004), and porcine bladder urothelial cells (Moriya et al., Journal of Urology, vol. 170, p. 2480-5, 2003). The Vacanti group also used the mesentery and interscapular fat pad to grow hepatocytes, intestinal cells and pancreatic islet cells in mice and rats (Vacanti et al., Journal of Pediatric Surgery, vol. 23, p. 3-9, 1988). Recently, a successful human clinical trial has been reported (Atala et al., Lancet, vol. 367, p. 1241-6, 2006; US Pat. appl. 20070059293 A1 by Atala). Autologous bladder cells were seeded on a biodegradable bladder-shaped scaffold made of collagen and polyglycolic acid, which was then implanted covered with omentum into the patients with myelomeningocele. In all of the above studies, the omentum was used as a single layer attached to one side of a flat scaffold, or wrapped around a three-dimensional scaffold.

Due to the problems listed above and despite the extensive research described above, tissue engineering on non-vascularized scaffolds has reached a major obstacle in developing organ structures greater than a few mm in size. Since most organs are larger than this, a better scaffold is needed. The present inventors set forth to address this important unmet need.

SUMMARY OF THE INVENTION

The present invention provides a novel method for producing tissue or organ in a mammal by implanting in vivo a novel three dimensional biodegradable scaffold.

One aspect of the present invention is a novel three dimensional biodegradable scaffold, said scaffold comprising a biodegradable or non-degradable polymer. This scaffold is designed to accommodate multiple layers of omentum.

Another aspect of the present invention is a procedure of implanting a three dimensional biodegradable scaffold in vivo, wherein said procedure comprises creating subcutaneous, intra-thoracic and intra-abdominal growth chambers.

Another aspect of the present invention is a method of implanting cells and/or tissues into a three dimensional biodegradable scaffold.

DETAILED DESCRIPTION OF THE INVENTION

Figure 1:
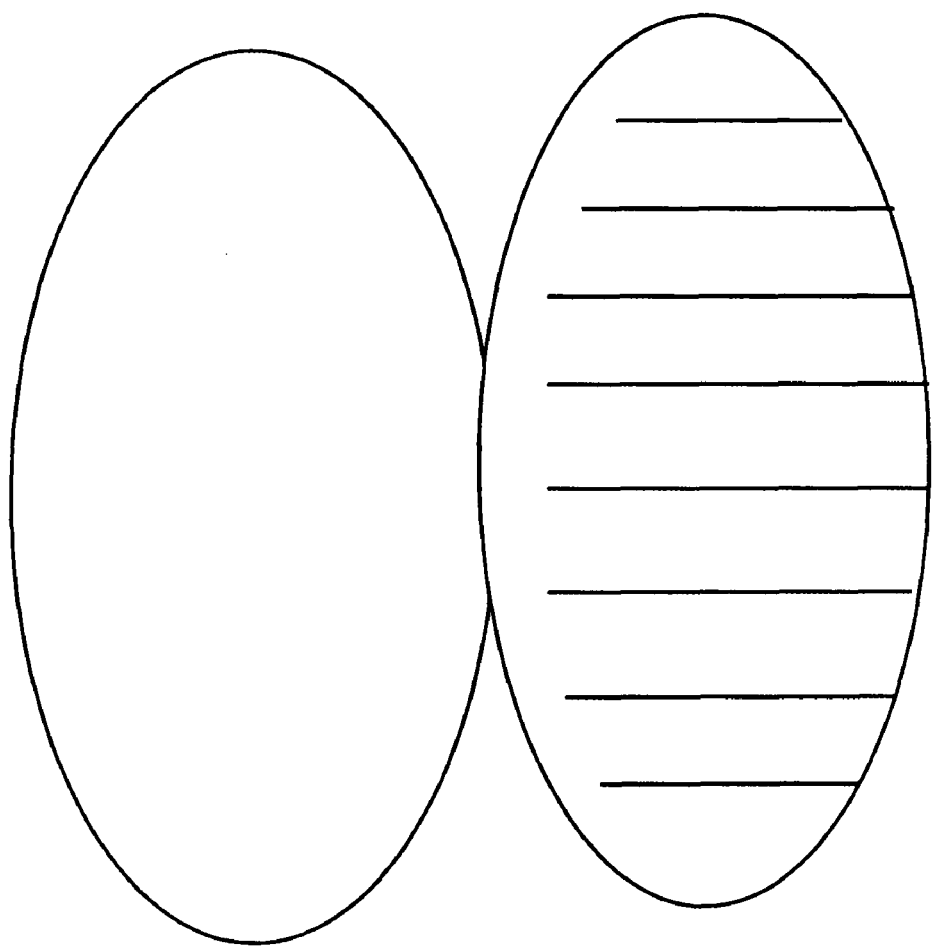
FIG. 1 is a schematic of a three dimensional scaffold design.
Figure 1:
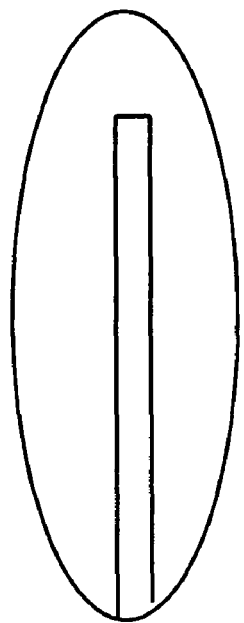
Figure 2:
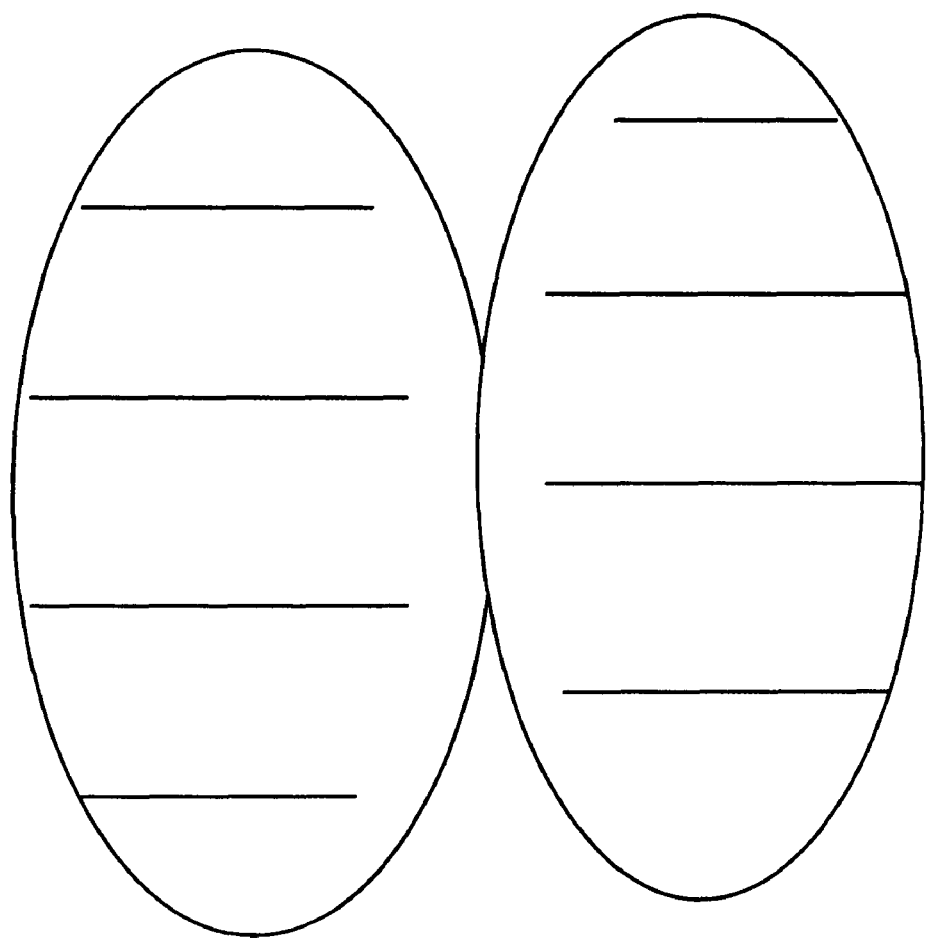
FIG. 2 is a schematic of alternative three dimensional scaffold design.
Figure 2:
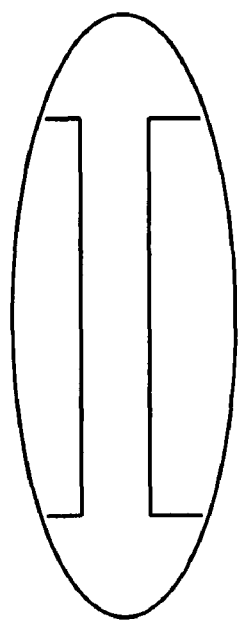
Figure 3:
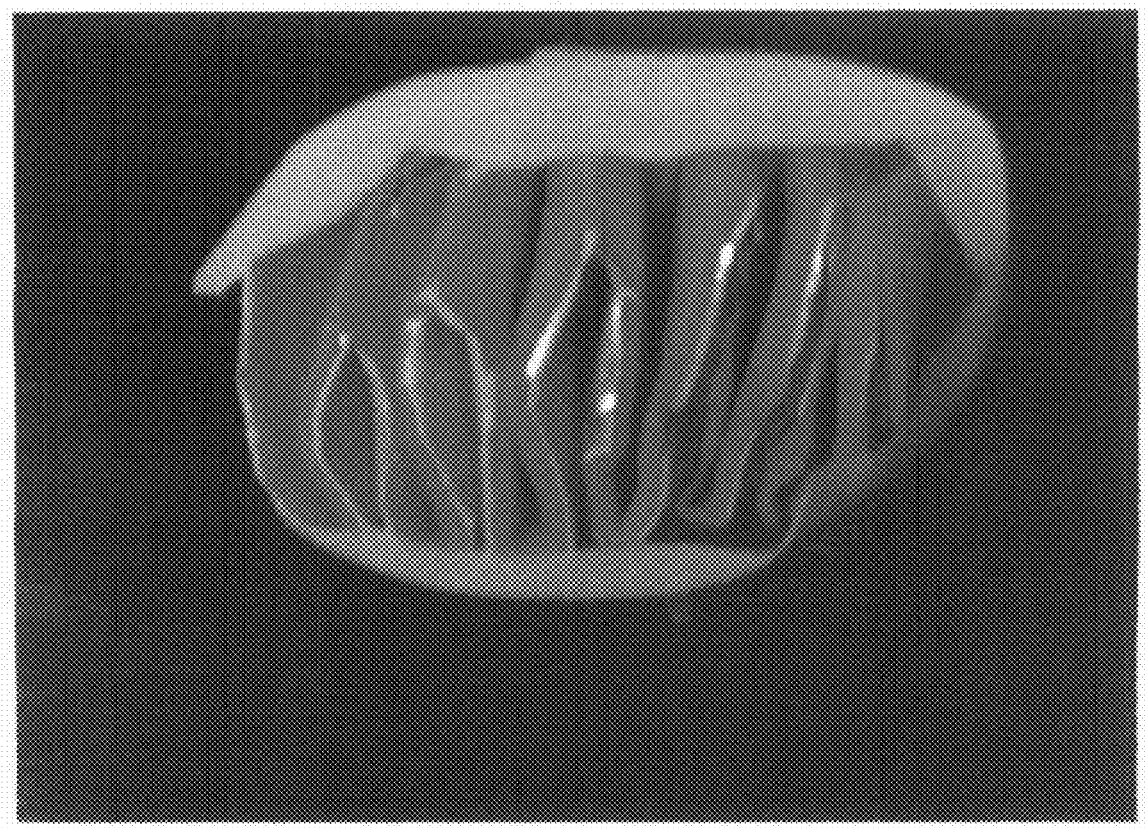
FIG. 3 is a prototype model showing the resulting omentum shaped inside the scaffold. The cells or tissues being engineered are inserted in between the folds of the omentum.

In an effort to design a three dimensional biodegradable scaffold which could overcome the barrier of developing large organs with tissue engineering, the present inventors hypothesized that a vascularized scaffold with a complete vascular bed would be needed to overcome this barrier. Specifically, the present inventors hypothesized that prior to cell seeding of the scaffold, a complete vascular bed should exist with a large inflow artery (2-3 mm), large outflow vein (3-4 mm) connected to a pre-existing capillary network.

The present invention thus provides a novel three dimensional biodegradable scaffold capable for use in developing large organs with tissue engineering. The scaffold interior is designed in order to accommodate multiple layers of omentum, in contact with autologous cells suspended in nutrient-containing matrix. The outer shape of the scaffold may be designed according to the shape of the intended defect/organ. For example, for a breast, the shape may resemble that of a standard breast implant. The scaffold may further comprise a subcutaneous port for the subsequent administration of additional cells, nutrients, drugs, etc.

Developing a scaffold in vitro with a complete vascular bed perfused with oxygenated blood is technically difficult and exponentially increases the complexity of tissue engineering. For this reason, attempts at developing in vitro models of vascularized scaffolds has not been seriously pursued. On the other hand, many studies have been done with in vivo models where vascularized tissue has been seeded with cells. A few examples of in vivo cell transplantation include: a) dopaminergic cell seeding of the brain for Parkinsonism; b) myoblast cell seeding of the heart for heart failure; c) spinal cord cell seeding for spinal cord injury; d) islet cell seeding for diabetes; and e) bladder cell seeding for bladder disease.

In all of these models, however, the cell seeding occurred in the existing organ that was already damaged by previous injury. Scar tissue, surgery, trauma, or ischemia have already taken their toll. And, importantly, most all of these in vivo cell infusions were "one time" procedures that could not be easily done outside of the operating room.

With the above technique of cell seeding, other tools available for in vitro tissue engineering cannot be done. These include growth medium infusion, additional cell seeding, and growth factor therapy administration. The present inventors propose that these tissue culture tools could be used in vivo if there was a growth chamber present in the in vivo model. Specifically, we need a growth chamber in the human body with its own fully developed vascular bed that would serve as the scaffold for cell growth.

The present inventors thus considered the following locations for the growth chamber: 1) subcutaneous space chamber; 2) intra-thoracic growth chamber; and 3) intra-abdominal growth chamber. Each option is described in more detail below.

1. Subcutaneous Space Chamber.

Non-vascularized subcutaneous space chambers have been well described, developed, and used for many different applications. Vascularized subcutaneous space chambers have not been well described or developed, however. The present inventors propose a subcutaneous space chamber which may be the best model for endocrine, paracrine, nerve, and nerve tissue engineering, since access is the easiest.

Potential sites for such a subcutaneous chamber would include the following, listed with their proposed vascular scaffold named by their blood supply:

| Growth Chamber Site | Vascular Scaffold (Blood supply) | Organ Size |
|---|---|---|
| Mid-abdomen | Deep inferior epigastric artery & vein | 50-1000 gm |
| Inguinal region | Superficial inferior epigastric a. & v. | 50-300 gm |
| Axillary region | Subscapular tree: circumflex scapular a. & v. OR thoracodorsal a. & v. | 50-100 gm |
| Medial thigh | Medial femoral circumflex a. & v. | 50-200 gm |

In each of these sites, the vascular supply would be dissected out, leaving the named blood vessels attached to the fat. This vascularized fat would be the scaffold. The scaffold would be inserted into a clam-shell shaped resorbable growth chamber and buried under the skin. The accessory ports, designed like a port-a-cath would be used to percutaneously infuse saline, growth media, cell suspensions, growth factors and would allow for aspirations to do assays of the growth chamber's metabolic activity. Once ultrasound or MRI scans confirmed that the full organ size had grown in the chamber, the organ would be moved to its final location and the vascular blood supply immediately re-established using microvascular techniques.

2. Intra-Thoracic Growth Chamber.

Developing a growth chamber in the pleural cavity or the mediastinum is feasible, but not practical. However, the present inventors believe that a vascularized substernal growth chamber could be developed without disturbing lung or cardiac function. The present inventors propose a substernal vascularized growth chamber which may be the best model for esophageal and tracheal tissue engineering.

The hypothesis is that in vivo engineering in the substernal position would allow for esophageal reconstruction once the engineered esophagus was complete. By placing it substernally, it would not have to be transferred to a new location for esophageal replacement. Instead, it could be connected to the cervical esophagus and to the stomach without a sternotomy or a thoracotomy.

The proposed substernal chamber could be designed as follows: 1) a vascularized skin tube would be developed on the abdominal wall with de-epithelialized skin lining the tube. The tube would be harvested on both superficial iliac circumflex arteries and transferred as a free flap with a double pedicle (one on each end); 2) the de-epithelialized skin tube would be either transferred to the substernal position at the initial surgery and revascularized in the neck and xiphoid regions with microsurgical techniques or it could be left as a tube on the abdominal wall and buried under abdominoplasty skin flaps. Regardless of the transfer timing, the tube would be protected on the outside by a cylindrical resorbable growth chamber. This chamber would have built in ports at each end for growth media infusion, cell seeding, growth factor therapy, and assay sampling. The chamber could also be designed with a window that would allow for endoscopy examination of the cell seeding success. For tracheal reconstruction, C-ring shaped cartilages could be implanted in the walls of the tube for tracheal support. These C-ring cartilages could be harvested from ribs and carved using standard surgical techniques (from ear reconstruction) or they could be engineered from cartilage cells grown on scaffolds in the laboratory; and 3) once there was endoscopic or radiologic confirmation of completed organogenesis, the engineered esophagus would be anastomosed to the native cervical esophagus and the stomach using standard thoracic surgery techniques. Post operative monitoring could be done with upper endoscopy. In the case of tracheal reconstruction, the engineered trachea would be left attached to its cervical blood supply and rotated posterior to the carina via a median sternotomy. The cervical end of the engineered trachea would be connected to the larynx or cricoid cartilage.

3. Intra-Abdominal Growth Chamber.

The abdominal cavity is a large, expandable, and easily accessible by laparoscopy for placing a growth chamber. The second major advantage is the presence of the omentum which could be used as the vascularized scaffold for the growth chamber. Placing the growth chamber in the peritoneal cavity could lead to adhesions, bowel obstruction, and growth chamber migration, however. For this reason, the present inventors propose an extraperitoneal position for the growth chamber and laparoscopic placement of the omentum in the growth chamber as the vascular scaffold. The present inventors hypothesize that this may be the best model for tissue engineering the following organs: a) autologous breast implant engineering; b) autologous long bone engineering; c) autologous cranial bone engineering; and d) autologous vascularized complete ear cartilage engineering.

The present inventors hypothesize that while omentum based vascularized growth chamber may be more difficult to develop than the subcutaneous growth chamber, it has the most promise for many translational research applications. Rationale for this optimism include the following: 1) the omentum is a naturally occurring, expendable vascular scaffold that has been show to develop a rich capillary network. Despite the fact that it is only fat, lymphatics, and blood vessels, it has been used to revascularize ischemic areas, treat lymphedema, and cover the heart after sternal debridements; 2) the omentum has long vascular pedicles that will allow for remote recipient vessel anastomosis. This eliminates the need for scars directly over the desired transplant location. For example, for the breast, the anastomosis can be done in the axilla or the omentum can be left attached to the greater curvature of the stomach; and 3) the omentum as a dual blood supply. This means that it can be split into two separate sections. This would allow us to develop two vascularized growth chambers in the extra-peritoneal space. This would make it ideal for both breast augmentation and breast reconstruction tissue engineering, since two breasts could be made.

In this model, the growth chamber would be inserted between the posterior rectus sheath and the anterior parietal peritoneum. This could be done using laparoscopic techniques. Through one port in the growth chamber, the omentum would be pulled into the growth chamber using laparoscopic instruments. Fixation of the omentum could be done with laparoscopic suture techniques or clips. The growth chamber would have one or more accessory ports designed like a port-a-cath for growth media infusion, cell seeding, growth factor therapy, and assay sampling. Since the chamber would be filled with fluid-like matrix and omental fat, ultrasound transducers could be used to percutaneously follow the growth of fat, since fat and fluid have contrasting echo shadows on ultrasound. Once ultrasound had confirmed that the chamber was completely filled with fat, the chamber would be transferred to the breast as a breast implant. The blood supply to the omentum could be left attached to the gastroepiploic vessels or it could be disrupted and revascularized to the axilla using microvascular techniques.

The present invention also describes the development of a resorbable, transferable shell for the proposed growth chamber. Recent developments in resorbable plate and screw technology for bone fixation has revolutionized craniofacial surgery. Non-absorbable titanium plates and screws caused permanent scar tissue and would migrate into the meninges with brain growth resulting in seizures. Today, craniofacial surgery is done with resorbable plates that take 18 months to absorb (Macropore, Lactosorb, etc.). These biopolymers are easily shaped with heat and can be easily made into chambers. No resorbable chambers made out of these biopolymers has been made to date however. The present inventors propose developing a slowing resorbable growth chamber with the following features: 1) make the growth chamber in the shape of the desired organ; 2) make a port (opening) to introduce a pedicled vascular scaffold existing of an artery, vein and a capillary network within the fat of the scaffold; and 3) make one or more additional ports for introducing growth media, cell suspensions, saline, growth factors, and gene therapy.

The resorbable chamber would allow the developing organ to be left in its "manufacturing site" but then could be transferred with the omental vessels using free microvascular tissue transfer techniques. This way the organ could be transferred on its vascular supply to the leg (bone), chest wall (breast), brain (dopaminergic cells), mediastinum (esophagus and trachea), only after it was confirmed that the organ was fully developed and functioning. Developing these resorbable chambers could be used for an unlimited variety of tissue engineering translational research.

The following example is provided to describe the invention in further detail.

Example 1

Figure 4:
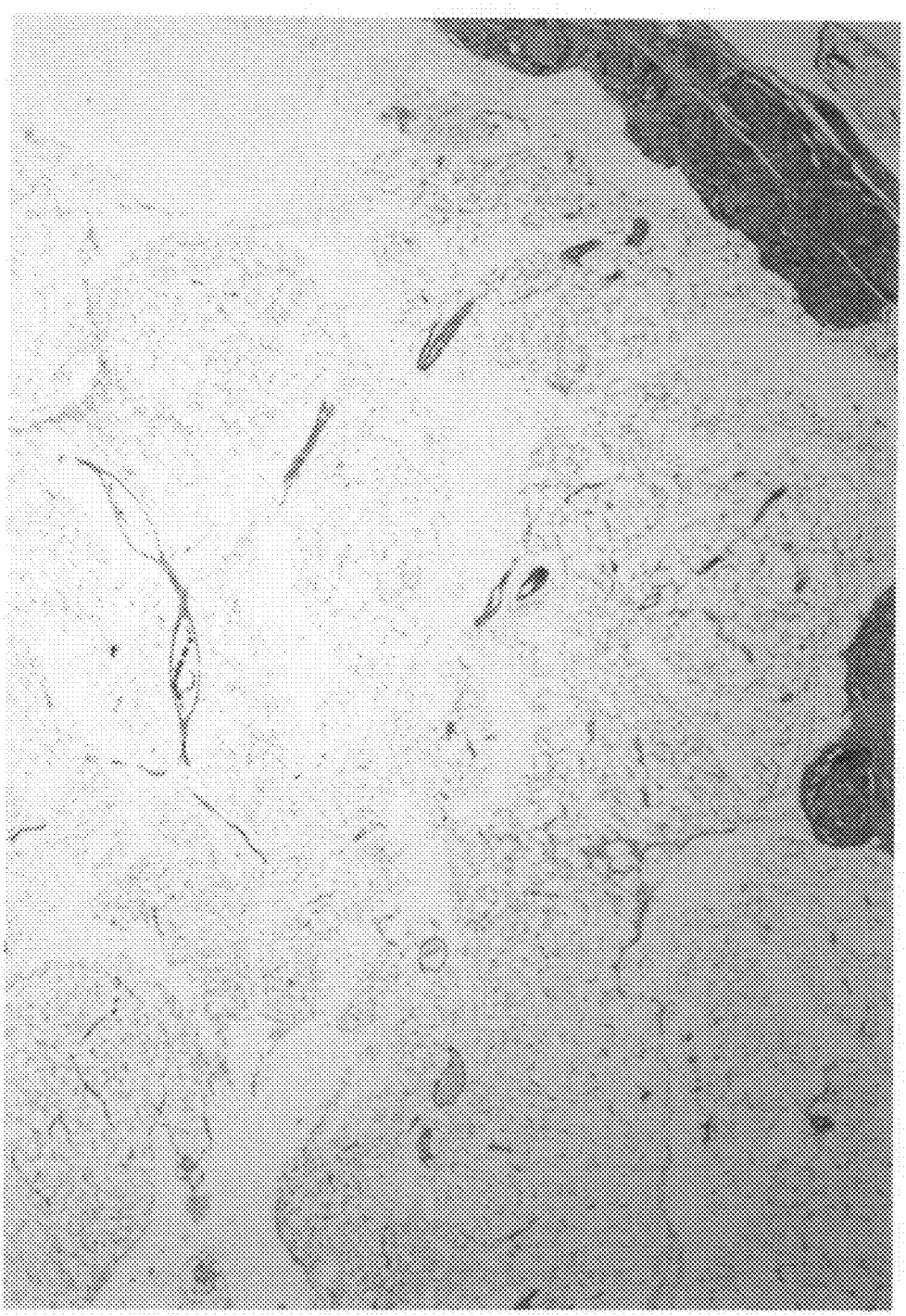
FIG. 4 is a photograph of well-vascularized fat tissue inside a biodegradable mesh scaffold, under the microscope at 20× magnification.
Figure 5:
FIG. 5 is a photograph of well-vascularized fat tissue inside a biodegradable mesh scaffold, under the microscope at 100× magnification.

This Example describes preliminary studies wherein the experiments were carried out in Sprague Dawley male rats at approximately 3.5 months in age. Under general anesthesia, an incision was made in the inguinal region of the rat, and its fat tissue was harvested. This fat tissue was then manually mixed with PuraMatrix (Becton Dickinson, Bedford, Mass.) in 10% sucrose solution. The fat tissue mixture was placed inside a biodegradable mesh pocket, and secured shut with sutures. A midline laparotomy incision was made in the same individual rat, its omentum was identified and wrapped around the mesh pocket, and secured with sutures. The rats tolerated the surgery well, and recovered without any complications. Four weeks later, the rats were sacrificed. The mesh pockets with fat inside were placed in paraffin, and H&E stained slides were generated. The results demonstrated that the fat tissue inside the mesh pocket survived and was well vascularized. The thickness of the fat tissue ranges from 2-6 mm. FIGS. 4 and 5 show well vascularized fat tissue at 20× and 100× magnification, respectively. In other experiments, the harvested fat tissue is placed immediately adjacent to the omentum, and the mesh is wrapped outside both fat and omentum. Both fat and omentum are incorporated into well vascularized fatty tissue with thickness ranging from 4-10 mm at four weeks.

What is claimed is:

1. An implant comprising: a three dimensional scaffold shell having an interior and an exterior; and a tissue matrix deposited in the interior of said scaffold shell comprising multiple folds of vascularized omentum in combination with excised fat tissue inserted between said folds of said omentum, wherein said scaffold is comprised of a material that is different from said tissue matrix.

2. An implant as recited in claim 1, wherein said implant is a breast implant.

3. An implant as recited in claim 1, wherein said fat tissue is present as a mixture of fat cells harvested from an organ and a nutrient.

4. An implant as recited in claim 1, wherein said scaffold is comprised of a polymer.

5. A method of generating an implant comprising a three dimensional scaffold shell containing a tissue matrix within its interior, the method comprising: providing a cell mixture comprising cells harvested from an organ, wherein the cells are immunocompatible with a subject; identifying a growth site in the subject comprising a vascular tissue having an arterial flow and a venous flow and a capability of growing the cell mixture; introducing a three dimensional scaffold into said growth site of said subject by placing said vascular tissue present in the growth site into the interior of said three dimensional scaffold shell, wherein the arterial and venous flow between said vascular tissue and said subject remain intact when said vascular tissue is placed into the interior of said scaffold shell; introducing the cell mixture into said interior of said scaffold shell, wherein the cell mixture associates with said vascular tissue in the interior of said scaffold shell; allowing said scaffold shell comprising said vascularized tissue and said cell mixture to incubate in said growth site to form an implant comprising said three dimensional scaffold shell comprising a tissue matrix within its interior; and removing said implant from said growth site.

6. A method according to claim 5, wherein said organ is a breast.

7. A method according to claim 5, wherein said vascularized tissue comprises omentum of a said patient.

8. A method according to claim 5, wherein said cell mixture comprises a mixture of fat cells and a nutrient.

9. A method according to claim 5, wherein the growth site is present in a region of the subject that is selected from the group consisting of the mid-abdomen region, an inguinal region, an axillary region, a medial thigh region, and the substernal region.

10. A method according to claim 5, wherein the three dimensional scaffold shell is bioresorbable.

* * * * *